(12) United States Patent
Ratron

(10) Patent No.: US 10,695,185 B2
(45) Date of Patent: *Jun. 30, 2020

(54) DETERMINING IMPLANTATION CONFIGURATION FOR A PROSTHETIC COMPONENT OR APPLICATION OF A RESURFACING TOOL

(71) Applicant: TORNIER, Montbonnot-Saint-Martin (FR)

(72) Inventor: Yves-Alain Ratron, Grenoble (FR)

(73) Assignee: TORNIER, Montbonnot-Saint-Martin (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/226,523

(22) Filed: Dec. 19, 2018

(65) Prior Publication Data

US 2019/0117404 A1 Apr. 25, 2019

Related U.S. Application Data

(60) Division of application No. 15/401,640, filed on Jan. 9, 2017, now Pat. No. 10,195,036, which is a
(Continued)

(30) Foreign Application Priority Data

Jan. 27, 2010 (FR) .................................. 10 50541

(51) Int. Cl.
*A61F 2/30* (2006.01)
*A61F 2/40* (2006.01)
(Continued)

(52) U.S. Cl.
CPC .......... *A61F 2/30942* (2013.01); *A61B 5/103* (2013.01); *A61B 5/4519* (2013.01);
(Continued)

(58) Field of Classification Search
CPC ...... A61F 2002/4627; A61F 2002/4666; A61F 2/2411; A61F 2/4657; A61F 2/30942; A61F 2/4081; A61B 5/0488; G06F 17/16
See application file for complete search history.

(56) References Cited

U.S. PATENT DOCUMENTS

| 5,610,966 A | 3/1997 | Martell et al. |
| 6,385,475 B1 | 5/2002 | Cinquin et al. |

(Continued)

FOREIGN PATENT DOCUMENTS

| EP | 1 249 213 | 10/2002 |
| EP | 1 563 810 | 8/2005 |

(Continued)

OTHER PUBLICATIONS

European Search Report issued in EP Application No. 10191949, dated Apr. 14, 2011, 9 pages.
(Continued)

*Primary Examiner* — Jason-Dennis N Stewart
(74) *Attorney, Agent, or Firm* — Knobbe, Martens, Olson & Bear LLP

(57) ABSTRACT

Systems and methods for modifying a shoulder joint configuration exhibiting wear that take into account resultant of forces responsible for the wear of the glenoid surface from geometric characteristics of wear.

10 Claims, 3 Drawing Sheets

Related U.S. Application Data continuation of application No. 14/885,363, filed on Oct. 16, 2015, now Pat. No. 9,575,931, which is a continuation of application No. 12/954,420, filed on Nov. 24, 2010, now Pat. No. 9,211,199.

(60) Provisional application No. 61/264,027, filed on Nov. 24, 2009.

(51) Int. Cl.
  *A61B 5/103* (2006.01)
  *A61B 5/00* (2006.01)
  *A61B 90/00* (2016.01)
  *A61F 2/46* (2006.01)
  *G06F 17/16* (2006.01)
  *A61F 2/48* (2006.01)
  *A61B 34/10* (2016.01)
  *A61B 34/20* (2016.01)

(52) U.S. Cl.
  CPC ............ *A61B 5/4528* (2013.01); *A61B 90/36* (2016.02); *A61F 2/4081* (2013.01); *A61F 2/4657* (2013.01); *G06F 17/16* (2013.01); *A61B 5/0059* (2013.01); *A61B 5/6878* (2013.01); *A61B 34/10* (2016.02); *A61B 2034/105* (2016.02); *A61B 2034/2055* (2016.02); *A61F 2/40* (2013.01); *A61F 2002/30884* (2013.01); *A61F 2002/30902* (2013.01); *A61F 2002/30943* (2013.01); *A61F 2002/4007* (2013.01); *A61F 2002/4632* (2013.01); *A61F 2002/4633* (2013.01); *A61F 2002/4666* (2013.01); *A61F 2002/488* (2013.01); *Y10T 29/49718* (2015.01)

(56) References Cited

U.S. PATENT DOCUMENTS

| | | |
|---|---|---|
| 6,915,150 B2 | 7/2005 | Cinquin et al. |
| 7,799,077 B2 | 9/2010 | Lang et al. |
| 7,822,588 B2 | 10/2010 | Mueller et al. |
| 7,927,338 B2 | 4/2011 | Laffargue et al. |
| 8,682,052 B2 | 3/2014 | Fitz et al. |
| 8,932,361 B2 | 1/2015 | Tornier et al. |
| 9,211,199 B2 | 12/2015 | Ratron |
| 2004/0102866 A1 | 5/2004 | Harris et al. |
| 2004/0181144 A1 | 9/2004 | Cinquin et al. |
| 2005/0049709 A1 | 3/2005 | Tornier |
| 2005/0065628 A1 | 3/2005 | Roose |
| 2005/0197814 A1 | 9/2005 | Aram et al. |
| 2007/0089518 A1 | 4/2007 | Ericson et al. |
| 2007/0191741 A1 | 8/2007 | Tsai et al. |
| 2008/0140209 A1 | 6/2008 | Iannotti et al. |
| 2008/0243127 A1 | 10/2008 | Lang et al. |
| 2009/0226068 A1 | 9/2009 | Fitz et al. |
| 2009/0264894 A1 | 10/2009 | Wasielewski |
| 2015/0105787 A1 | 4/2015 | Tornier et al. |
| 2016/0038250 A1 | 2/2016 | Ratron |

FOREIGN PATENT DOCUMENTS

| | | |
|---|---|---|
| EP | 1 862 151 | 12/2007 |
| EP | 2 135 576 | 12/2009 |
| FR | 2 579 454 | 10/1986 |
| FR | 2 859 099 | 3/2005 |
| WO | WO 02/061688 | 8/2002 |

OTHER PUBLICATIONS

French Opinion issued in FR Application No. 1050541, dated Jan. 27, 2010, 5 pages.

French Search Report issued in FR Application No. 1050541, dated Sep. 15, 2010, 2 pages.

Search Report issued in French Application No. 08 54092, dated Feb. 9, 2009, in 8 pages.

DETERMINING IMPLANTATION CONFIGURATION FOR A PROSTHETIC COMPONENT OR APPLICATION OF A RESURFACING TOOL

CROSS-REFERENCE TO RELATED APPLICATION

This application claims priority to U.S. Provisional Application No. 61/264,027, filed Nov. 24, 2009 and French Application No. FR 10 50541, filed Jan. 27, 2010, both of which are incorporated herein by reference in their entireties.

TECHNICAL FIELD

The present invention relates to a device and a method for determining an implantation configuration in a patient for a glenoid component of a shoulder prosthesis. It also relates to a device and a method for determining a configuration for application of a glenoid resurfacing tool.

BACKGROUND

Replacing the glenoid articular surface of the scapula of a human being with a glenoid component of a shoulder prosthesis is a delicate surgical operation, notably because of the muscular environment of the shoulder. It is found that, depending on the position of implantation of such a glenoid component, risks of separation of the component exist because of the forces applied to this component in subsequent movements of the prosthesized shoulder.

In particular, in certain patients, it was found that, even if the implantation on their scapula of such a glenoid component was perfectly centered on the articular head of the corresponding humerus on completion of the surgical implantation operation, the resumption of their activities led, more or less rapidly, to an instability of the prosthesis.

To circumvent this issue, US-A-2009/0226068 proposes manufacturing a "custom" glenoid component, the articular surface of which is conformed, in its design, by taking into account the wear observed on the socket to be prosthesized of a patient. Such an approach does, however, prove costly since it means customizing the glenoid component for each patient to be treated. Similar considerations are found for the glenoid resurfacing operations on the scapula.

SUMMARY

Some embodiments relate to methods for modifying a shoulder joint exhibiting wear on a glenoid surface, including methods and devices for optimizing either the implantation configuration of a glenoid component, or the configuration of a glenoid resurfacing tool, by taking into account the forces of muscular origin linked to a regular articular activity on the articulation of the prosthesized or resurfaced shoulder of a patient.

Some embodiments relate to methods including defining a spatial coordinate system of the scapula, providing mapping data relating to the glenoid surface of the scapula, the mapping data being defined in the spatial coordinate system, determining geometric characteristics of wear of the glenoid surface from then mapping data, determining the vector characteristics of a resultant of forces responsible for wear of the glenoid surface from the geometric characteristics of wear, and performing a desired modification of the shoulder joint using the vector characteristics of the resultant of forces to take into account an action of the resultant of forces on the articular cooperation between the scapula and a humerus of the patient.

Some embodiments relate to a systems including mapping means for providing mapping data relating to a glenoid surface of a scapula of a patient, the mapping data being defined in a spatial coordinate system of the scapula and first determination means for determining geometric characteristics of wear of the glenoid surface from the mapping data supplied by the mapping means. The systems also include second determination means for determining the vector characteristics of a resultant of forces responsible for the wear of the glenoid surface from geometric characteristics of wear supplied by the first determination means and third determination means for determining a modified shoulder joint configuration from the vector characteristics of the resultant of forces supplied by the second determination means by taking into account the action of the resultant of forces responsible for the wear of the glenoid surface on the articular cooperation between the scapula and the humerus of the patient.

Some embodiments relate to a device for determining a configuration in which either a glenoid component of a shoulder prosthesis is to be implanted on the scapula of a patient, or a glenoid resurfacing tool is to be applied to the scapula of a patient.

Other embodiments relate to a method for determining a configuration in which either a glenoid component of a shoulder prosthesis is to be implanted on the scapula of a patient, or a glenoid resurfacing tool is to be applied to the scapula of a patient. The method includes determining the positioning of a pre-existing glenoid component when the articulation of the shoulder of a patient is considered to be subject to forces of muscular origin linked to a regular activity of the patient, typically an articular activity that the patient repeats several times a day. In some embodiments, the method exploits data relating to the observed wear of the glenoid surface of the patient. In some embodiments, the method determines an implantation configuration for the glenoid prosthetic component by considering the positional influence of this resultant of forces on the articular cooperation between the scapula and the humerus of the patient.

In some embodiments, the method can be applied to a glenoid component of a total shoulder prosthesis, where the head of the humerus of the patient is to be prosthesized with a humeral component of the shoulder prosthesis. In other embodiments, the method can be applied to a glenoid prosthetic component intended to be articulated directly on the natural articular head of the humerus of the patient. The method can be used with glenoid components whose articular face is concave or glenoid components with a convex articular face.

In some embodiments, the method and device can be used for positioning of a milling tool on the scapula for resurfacing the scapula. In some embodiments, the method is performed preoperationally using ad hoc calculation and simulation means. As for the result of this method, it can be used subsequently, in a subsequent surgical operation aiming effectively to implant a glenoid component or to apply a glenoid resurfacing tool.

In conjunction with the invention, there is proposed a surgical method for implanting in a patient a glenoid component of a shoulder prosthesis, in which:

a preferred position of implantation of the glenoid component is determined in accordance with the determination method as defined above, the scapula of the patient is identified in space, with a one-to-one link with the spatial coordinate system defined in the determination method, and the glenoid component is fitted on the scapula of the patient according to the preferred position of implantation.

Advantageously, at least a portion of the mapping data are acquired by palpation of the scapula of the patient.

Also in conjunction with the invention, there is proposed a surgical method for glenoid resurfacing of the scapula of a patient, in which:

a preferred position of application of a resurfacing tool is determined in accordance with the determination method as defined above, the scapula of the patient is identified in space, with a one-to-one link with the spatial coordinate system defined in the determination method, and the glenoid surface of the scapula is honed by applying to the latter the resurfacing tool according to the preferred position of application.

Advantageously, at least a portion of the mapping data are acquired by palpation of the scapula of the patient.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

As previously noted, the drawings are to be regarded as illustrative in nature and not restrictive.

DETAILED DESCRIPTION

Various embodiments related to methodology and systems for modifying a shoulder joint configuration, including determining an implantation position of a glenoid component on a scapula or a resurfacing process for the glenoid, by taking account of the muscular environment of the shoulder.

Figure 1:
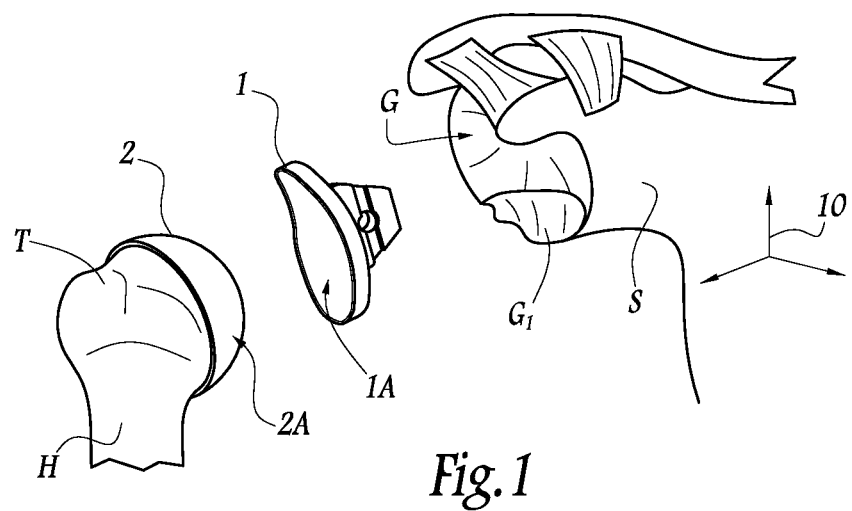
FIG. 1 is an exploded, perspective schematic view of the shoulder of a patient, associated with prosthetic components of a shoulder prosthesis, according to some embodiments.
Figure 2:
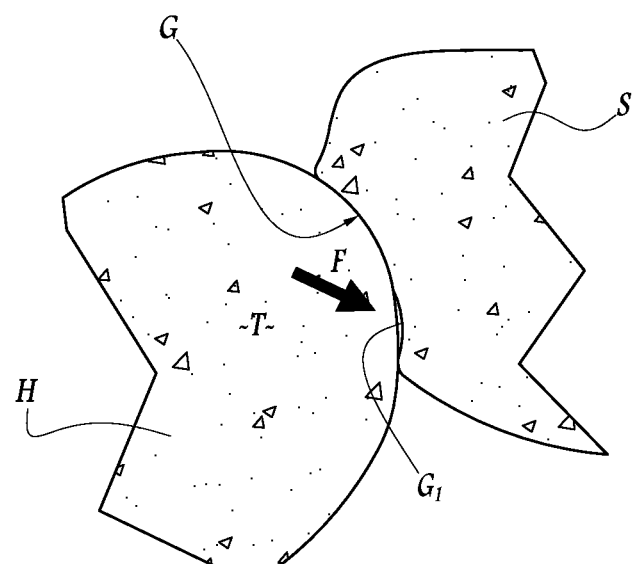
FIG. 2 is a schematic cross section of an unprosthesized shoulder, according to some embodiments.

FIGS. 1 and 2 show, partly, a shoulder of a patient, comprising a scapula S and a humerus H. The scapula S delimits, on its lateral side facing the humerus H, a glenoid surface G. In the natural state of the shoulder, the head T of the humerus H bears in an articulated manner against the glenoid surface G. In a manner not represented in the figures, the articular cooperation between the scapula S and the humerus H is controlled by muscles extending between the scapula and the humerus, in particular the deltoid muscle and the rotator cuff muscles. Hereinafter, the expression "muscular environment" is used to designate a musculature including the abovementioned muscles.

Figure 3:
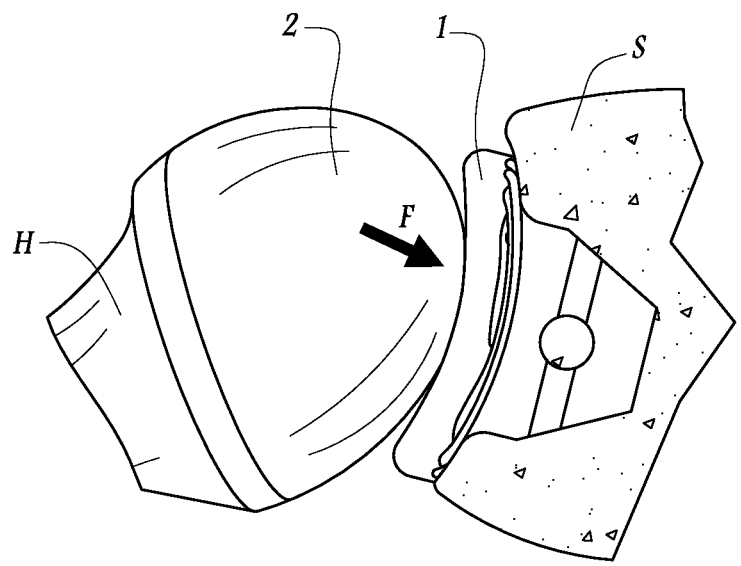
FIGS. 3 and 4 are views similar to FIG. 2, showing in elevation two different implantation configurations of the shoulder prosthesis of FIG. 1, according to some embodiments.
Figure 4:
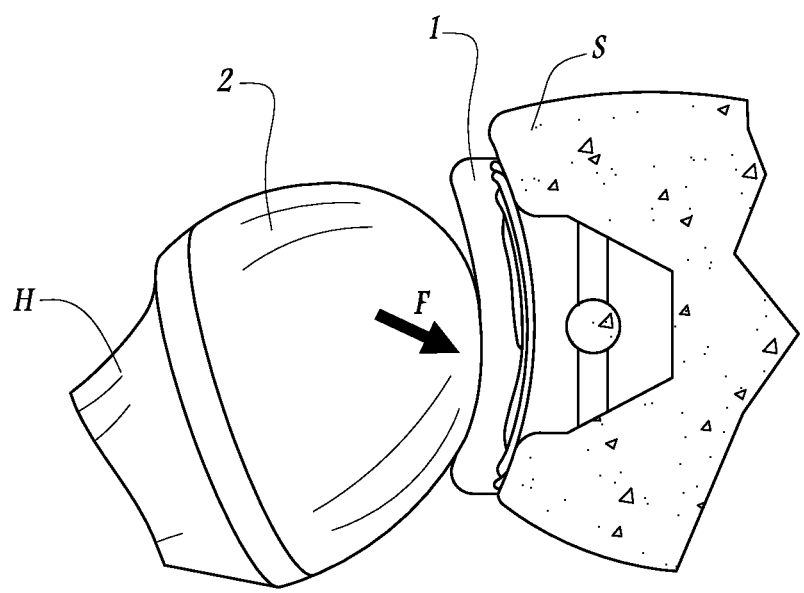

FIGS. 1, 3 and 4 schematically represent a shoulder prosthesis comprising a glenoid component 1 and a humeral component 2. In the nonlimiting example considered here, the glenoid component 1 and humeral component 2 have respective overall cup portion shapes, delimiting respective articular faces 1A and 2A that are geometrically complementary to one another so that these components articulate with one another.

Some embodiments described herein relate to methods for determining an implantation configuration for the glenoid component 1 on the scapula S, by taking account of the muscular environment of the shoulder. In some embodiments, data relating to the anatomical geometry of the scapula S is initially available or acquired preoperatively. The data is used to draw up a three-dimensional map of the glenoid surface G of this scapula, after having defined a spatial coordinate system 10 of the scapula S. The spatial coordinate system 10 is, for example, established using noteworthy natural identification points of the scapula S.

In some embodiments, the mapping data relating to the natural geometry of the glenoid surface G is extracted from preoperational images of the scapula S, for example from scanner images. FIG. 2 is a cross sectional representation of the shoulder that corresponds to such a preoperational image.

In some embodiments, the wear of the glenoid surface G is characterized from the mapping data. Thus, as shown in FIGS. 1 and 2, the glenoid surface G has, in its bottom portion and in all its anteroposterior dimension, a worn region $G_1$, seen in cross section in FIG. 2. Although the worn region $G_1$ is shown in the bottom, it should be noted that glenoid wears are often observed in the upper portion of the glenoid surface.

In some embodiments, the worn region $G_1$ is characterized by its geometric characteristics as assessed relative to the remainder of the glenoid surface G. For example, the worn region $G_1$ is optionally characterized by the dimensions of its peripheral outline in the three directions of the coordinate system 10, by its depth gradients in the coordinate system 10, and by other additional or alternate features as appropriate. As described in greater detail, these geometric characteristics of wear are chosen so as to help identify the mechanical causes behind the wear of the glenoid surface G.

To determine the geometric characteristics of wear of the glenoid surface G, a number of possibilities are contemplated. In some embodiments, determination of the geometric characteristics of wear includes using means for comparing the previously-obtained mapping data relating to the glenoid surface G to data relating to the anatomy of a reference glenoid surface, the data comparison being supplied by a pre-existing database—i.e., one that is generated prior to the surgical replacement procedure, or preoperatively. The means optionally include hardware, software, and computer implemented algorithms adapted for comparing the previously-obtained mapping data relating to the glenoid surface G to data relating to the anatomy of a reference glenoid surface.

Some embodiments include, computer modeling of a theoretical glenoid surface on the basis of the mapping data relating to a portion of the glenoid surface G that is considered to not be worn by using shape recognition algorithms and pre-established genetic and morphometric data. The remaining mapping data relating to the worn region $G_1$ is then compared to the theoretical glenoid surface.

In some embodiments, the geometric characteristics of wear of the glenoid surface G are used in a subsequent step to estimate the forces responsible for the formation of the worn region $G_1$. In practice, the appearance and the trend of the worn region $G_1$ within the glenoid surface G are the consequence of the regular and repetitive action of a certain configuration of the muscular environment of the shoulder of the patient. In other words, because of a regular articular activity of the patient (movements the patient repeats frequently in the context of everyday life), the muscular environment of the shoulder applies to the scapula S and to the humerus H repeated stresses which, in the long term, lead to the appearance and the development of wear of the glenoid surface G in the region $G_1$. This action of the muscular environment may be represented by a resultant of forces, denoted F in FIG. 2, whose vector characteristics are determined from geometric characteristics of wear of the glenoid surface G.

In some embodiments, to identify the vector characteristics of the resultant of forces F from the geometric characteristics of wear of the glenoid surface G, use is advantageously made of a pre-existing shoulder musculoskeletal model. The biomechanical model is optionally used to simulate the articular movements of the shoulder by quantifying the forces in the articulation between the scapula and the humerus of the shoulder and in the muscular environment of the shoulder. The shoulder musculoskeletal model is optionally used to construct a wear database—where several glenoid wears are simulated within the model, each wear being simulated under the action of different corresponding predetermined forces of articulation. Some embodiments include using comparison means, such as hardware, software, and computer-implemented algorithms for comparing the geometric characteristics of wear of the glenoid surface G to the duly pre-established wear database generated with the biomechanical model to approximate the vector characteristics of the resultant of forces F.

Finally, in some embodiments, means are provided in the form of computer-implemented algorithms, hardware, and software to use the vector characteristics of the resultant of forces F to determine an optimal position of implantation of the glenoid component 1 on the scapula S such that, in subsequent service, the glenoid component 1 opposes the resultant of forces F. In other words, account is taken of the action of this resultant of forces F on the future articular cooperation between the glenoid component 1 and the humeral component 2, according to the relative implantation configuration of these components within the shoulder of the patient. According to some embodiments, the shoulder musculoskeletal model is used again to simulate the articulation between the scapula S and the humerus H subject to muscular forces corresponding to the resultant of forces F and then to calculate, in the coordinate system 10, the geometric characteristics of a position of implantation of the glenoid component 1 so that the relative mobility between the glenoid component 1 and the humeral component 2 is balanced under the effect of the resultant of the forces F. In some embodiments, this balancing is advantageously determined so that, during movements of the prosthesized shoulder producing forces of resultant F, the articular contact region between the scapula S and the humerus H is substantially centered relative to the peripheral outline of the glenoid component, and not offset toward a peripheral portion thereof as shown in FIG. 3.

Thus, the abovementioned geometric characteristics, relating to the position of implantation of the glenoid component 1, help quantify the positioning parameters with respect to the scapula S in the coordinate system 10, namely the height of the positioning parameters in the three directions of the coordinate system and the inclination of the positioning parameters in the three directions.

In some embodiments, the position of implantation of the glenoid component 1 determined in this way is shown in FIG. 3, which illustrates balancing between the glenoid component 1 and the humeral component 2 while the scapula S and the humerus H of the shoulder of the patient to be operated on are subjected to the effect of the resultant of forces F. Conversely, FIG. 4 illustrates another implantation configuration whereby the glenoid component 1 is placed without taking account of the resultant of forces F. In the case where the resultant of the forces F are not accounted for, unlike in FIG. 3, the position of the component 1 does not satisfactorily balance the action of the resultant F with the mobility of the prosthesized shoulder, such that, as soon as the patient resumes everyday activities, and each time the patient repeats the actions that led to the appearance of the worn region $G_1$ of the glenoid surface G, the shoulder prosthesis is stressed according to an unbalanced configuration between its components 1 and 2. Thus, where account is not taken of the effect of the resultant forces F, a significant long term risk of instability of the prosthesis exists.

On completion of the described methodology, and according to some embodiments, a preferred position of implantation of the glenoid component 1 on the scapula S is determined using hardware, software, and computer-implemented algorithms adapted to identify the preferred position of implantation according to, or otherwise taking into account, the action of the resultant of forces F on the articulation between the scapula and the humerus H of the patient to be prosthesized. As previously referenced, it should be emphasized that various steps of the method are optionally implemented outside an actual surgical intervention (i.e., preoperatively), without having to actually access the scapula S and the humerus H of the patient (e.g., via incisions in the soft parts surrounding these structures).

In practice, the implementation of the method for approximating the vector characteristics of the resultant of forces F and appropriate implantation position of the glenoid component 1 are assisted via computer means, for example including hardware, software, and computer-implemented algorithms adapted for carrying out the determination steps, relative positioning calculations, and simulation calculations previously referenced.

Figure 5:
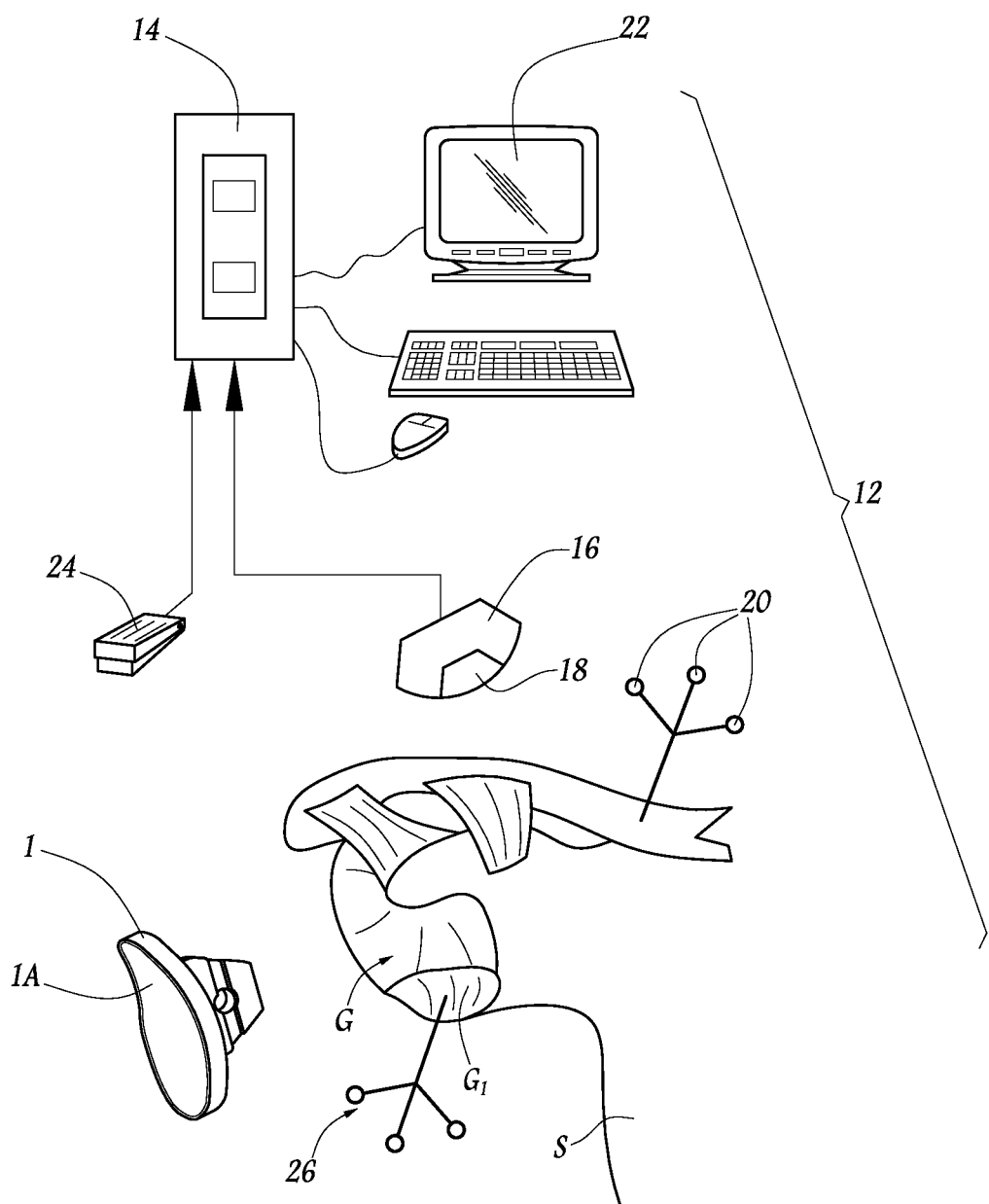
FIG. 5 is a schematic view of a system for implanting, in the patient, the glenoid component of the shoulder prosthesis, according to some embodiments.

In some embodiments, a surgeon uses the data relating to the preferred position of implantation of the glenoid component 1 in association with implantation of a surgical assembly 12 shown in FIG. 5. The assembly 12 includes a computer 14 associated with a unit adapted for sending and receiving infrared radiation, the unit including a sensor 16 linked to the computer and an infrared power source 18 covering the operational field in which the scapula S of the patient is represented. To assist the computer 14 with identifying the scapula S in space, the assembly 12 includes a group of markers 20 which return, passively, the infrared radiation toward the sensor 16. The group of markers 20 forms a three-dimensional marking system assisting the sensor 16 with following the position of the scapula in space. The computer 14 is also associated with a video screen 22 capable of displaying useful information to the surgeon, such as information relating to the identification of the scapula S and other data described below, preferably in graphic representation form. The assembly 12 also comprises control means 24, for example in the form of a pedal that can be actuated by the foot of the surgeon.

In some embodiments, implantation of the glenoid component 1 in the preferred position of implantation includes using the computer 14, including hardware, software, and computer-implemented algorithms, adapted to establish a one-to-one link between the space coordinates using the group of markers 20 and the coordinate system 10 used to implement the method for determining the preferred position of implantation. For this, the surgeon uses, as an example, a feeler 26 which is identified in space by the sensor 16. After incision of the soft parts of the shoulder of the patient, the surgeon brings this feeler 26 to a set of landmarks, or noteworthy places, of the scapula S which are then used to define the coordinate system 10 where, by actuation of the control pedal 24, the surgeon acquires the position of the feeler 26 and stores the position with the computer 14. Then, from the positional data, the computer 14 calculates the mathematical link between the coordinate system 10 (FIG. 1) and the spatial coordinates of the sensor 16, where the computer 14 includes hardware, software, and computer-implemented algorithms adapted for such purposes.

The surgeon then fits the glenoid component 1 on the scapula S according to the preferred position of implantation. In practice, the corresponding movements of the surgeon are advantageously guided by navigation means driven by the computer 14.

Optionally, after the surgeon has incised the soft parts of the shoulder of the patient, but before he begins to fit the glenoid component 1, the surgeon can exploit his access to the scapula S to collect mapping data relating to the glenoid surface G. The mapping data can complement or constitute all the mapping data used to implement the method for determining the preferred position of implantation of the glenoid component 1. As an example, the mapping data relating to the scapula S is thus obtained peroperationally using the feeler 26 brought to the glenoid surface G. In other words, in some embodiments, the determination method is implemented peroperationally, as opposed to other embodiments in which the method of acquiring mapping data was described as being preoperational.

Various arrangements and variants of the determination method and of the device, and of the surgical implantation method and of the assembly used to implement such methodology are contemplated. As examples:

the means of identifying the scapula S and/or the feeler 26 are not limited to infrared reflecting markers—markers sensitive to ultrasound or to electromagnetic fields, for example, can be additionally or alternatively used;

rather than the position of implantation of the humeral component 2 on the humerus H being predetermined, the position of implantation of the humeral component 2 can be adjusted concomitantly with the determination of an implantation configuration for the glenoid component 1;

the methodology and system for modifying a shoulder joint configuration is optionally implemented to determine a preferred implantation configuration for a glenoid component articulated directly on the natural head of the humerus H, without requiring the implantation of a humeral component such as the component 2; and/or the methodology and system for modifying a shoulder joint configuration is optionally implemented in the context of the glenoid resurfacing of the scapula S, with or without the subsequent fitting of a resurfacing implant; in such cases, rather than determining a position of implantation of the glenoid component 1, as described above, the invention is applied to determine a position of application of a resurfacing tool on the scapula, in order to hone its glenoid surface G so that the latter can then be better articulated with the head of the humerus H—that is to say, by taking account of the action of the resultant of forces F on this articulation, the considerations detailed hitherto regarding the determination of an implantation configuration for the glenoid component 1 apply by modifying the methodology to the determination of a positioning configuration for the resurfacing tool on the scapula.

Various additional or alternate modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A method for determining a configuration in which a resurfacing tool is applied to a scapula of a patient, the method comprising:

defining a spatial coordinate system of the scapula;

providing mapping data relating to a glenoid surface of the scapula, the mapping data being defined in the spatial coordinate system;

determining geometric characteristics of wear of the glenoid surface from the mapping data;

determining the vector characteristics of a force resultant of forces responsible for wear of the glenoid surface from the geometric characteristics of wear; and determining an application of the resurfacing tool on the glenoid surface of the scapula from the vector characteristics of the force resultant by taking into account action of the force resultant on the articular cooperation between the scapula as resurfaced by the application of the resurfacing tool and the humerus of the patient.

2. The method of claim 1, wherein determining the geometric characteristics of wear includes comparing the mapping data to data relating to a reference anatomy for a glenoid surface supplied by a pre-existing database.

3. The method of claim 1, further comprising modeling a theoretical glenoid surface from a portion of the mapping data, the portion of the mapping data selectively corresponding to a portion of the glenoid surface of the scapula, and wherein determining the geometric characteristics of wear includes comparing a remaining portion of the mapping data to the theoretical glenoid surface.

4. The method of claim 1, wherein determining the vector characteristics of the force resultant includes comparing the geometric characteristics of wear to pre-established wear data using a pre-existing shoulder musculoskeletal model.

5. The method of claim 4, wherein the pre-established wear data is obtained by simulating glenoid wear of the shoulder musculoskeletal model under the respective actions of corresponding predetermined forces.

6. The method of claim 1, wherein determining the application of the resurfacing tool is implemented so that the articular cooperation between the scapula as resurfaced by the application of the resurfacing tool and the humerus are balanced under the effect of a force conforming to the vector characteristics of the force resultant.

7. The method of claim 6, wherein determining the application of the resurfacing tool includes calculating, from a pre-existing shoulder musculoskeletal model, simulation of the articular cooperation between the scapula as resurfaced by the application of the resurfacing tool and the humerus, subjected to a force conforming to the vector characteristics of the force resultant.

8. The method of claim 6, wherein determining the application of the resurfacing tool includes calculating the geometric characteristics in the spatial coordinate system of the application of the resurfacing tool so that when the shoulder of the patient is stressed with a force conforming to the vector characteristics of the force resultant, an articular contact region between the scapula as resurfaced by the application of the resurfacing tool and the humerus is substantially centered relative to a peripheral outline of the resurfacing.

9. The method of claim 1, wherein at least a portion of the mapping data is acquired by palpation of the scapula.

10. The method of claim 1, wherein at least a portion of the mapping data is extracted from preoperational images of the scapula.

\* \* \* \* \*